United States Patent
Woollam et al.

(10) Patent No.: US 7,253,900 B1
(45) Date of Patent: Aug. 7, 2007

(54) ELLIPSOMETER OR POLARIMETER AND THE LIKE SYSTEM WITH MULTIPLE DETECTOR ELEMENT DETECTOR IN ENVIRONMENTAL CONTROL CHAMBER INCLUDING SECURE SAMPLE ACCESS

(75) Inventors: John A. Woollam, Lincoln, NE (US); Gregory K. Pribil, Lincoln, NE (US); Martin M. Liphardt, Lincoln, NE (US); James D. Welch, Omaha, NE (US)

(73) Assignee: J.A. Woollam Co., Inc., Lincoln, NE (US)

( * ) Notice: Subject to any disclaimer, the term of this patent is extended or adjusted under 35 U.S.C. 154(b) by 368 days.

(21) Appl. No.: 10/962,353

(22) Filed: Oct. 9, 2004

Related U.S. Application Data (63) Continuation-in-part of application No. 10/699,540, filed on Nov. 1, 2003, now Pat. No. 7,158,231.

(60) Provisional application No. 60/512,462, filed on Oct. 17, 2003, provisional application No. 60/473,615, filed on May 28, 2003.

(51) Int. Cl.
*G01J 4/00* (2006.01)

(52) U.S. Cl. ..................................... 356/364
(58) Field of Classification Search ............... None
See application file for complete search history.

(56) References Cited

U.S. PATENT DOCUMENTS

| | | | | |
|---|---|---|---|---|
| 4,053,232 A | 10/1977 | Dill et al. | .................. | 356/118 |
| 4,657,390 A * | 4/1987 | Doyle | .................. | 356/451 |
| 4,668,086 A | 5/1987 | Redner | .................. | 356/33 |
| 4,770,895 A | 9/1988 | Hartley | .................. | 427/10 |
| 4,875,773 A | 10/1989 | Burns et al. | .................. | 356/328 |
| 5,091,320 A | 2/1992 | Aspnes et al. | .................. | 437/8 |
| 5,329,357 A | 7/1994 | Bernoux et al. | .................. | 356/369 |
| 5,337,146 A | 8/1994 | Azzam | .................. | 356/367 |
| 5,373,359 A | 12/1994 | Woollam et al. | .................. | 356/328 |
| 5,504,582 A | 4/1996 | Johs et al. | .................. | 356/369 |
| 5,521,706 A | 5/1996 | Green et al. | .................. | 356/369 |
| 5,596,406 A | 1/1997 | Rosencwaig et al. | ....... | 356/327 |
| 5,666,201 A | 9/1997 | Johs et al. | .................. | 356/369 |
| 5,706,212 A | 1/1998 | Thompson et al. | ......... | 364/525 |
| 5,805,285 A | 9/1998 | Johs et al. | .................. | 356/369 |
| 5,818,596 A | 10/1998 | Imai et al. | .................. | 356/381 |
| 5,872,630 A | 2/1999 | Johs et al. | .................. | 356/369 |
| 5,877,859 A | 3/1999 | Aspnes et al. | .............. | 356/364 |
| 5,929,995 A | 7/1999 | Johs | .......................... | 356/369 |
| 5,973,787 A | 10/1999 | Aspnes et al. | .............. | 356/369 |
| 6,031,619 A | 2/2000 | Wilkens et al. | ............. | 356/419 |
| 6,034,777 A | 3/2000 | Johs et al. | .................. | 356/369 |
| 6,134,012 A | 10/2000 | Aspnes et al. | .............. | 356/369 |
| 6,320,657 B1 | 11/2001 | Aspnes et al. | .............. | 356/369 |

(Continued)

OTHER PUBLICATIONS

Beaslehole PCT WO 2004/070363, Publication Aug. 19, 2004.

(Continued)

*Primary Examiner*—Tu T. Nguyen
(74) *Attorney, Agent, or Firm*—James D. Welch (57) ABSTRACT

A spectrophotometer, ellipsometer or polarimeter or the like system with a spectroscopic source of wavelengths and a detector with multiple detector elements for simultaneous monitoring of a number of wavelengths in an environmental control chamber which optionally provides for secured sample entry, and methodology of use.

9 Claims, 6 Drawing Sheets

U.S. PATENT DOCUMENTS

| | | |
|---|---|---|
| 6,353,477 B1 | 3/2002 | Johs et al. ............ 356/369 |
| 6,414,302 B1 | 7/2002 | Freeouf ............ 250/225 |
| 6,493,097 B1 | 12/2002 | Ivarsson ............ 356/630 |
| 2002/0024668 A1 | 2/2002 | Stehle et al. |
| 2002/0149774 A1 | 10/2002 | Mc Aninch |
| 2003/0071996 A1 | 4/2003 | Wang et al. |
| 2003/0150997 A1 | 8/2003 | Ekert et al. |
| 2004/0156049 A1* | 8/2004 | Breninger et al. ......... 356/364 |

OTHER PUBLICATIONS

V U V-Vase Flyer.

"A New Purge UV Spectroscopic Ellipsometer to Characterize Thin Films and Multilayers at 157nm", Boher et al., Proc. SPIE, vol. 3998, (Jun. 2000).

"Characterisation of Thin Films and Multilayers in the VUV Wavelength Range Using Spectroscopic Ellipsometry and Spectroscopic Photometry", Boher et al., 157nm Symposium, (May 2000).

"Progress in Spectroscopic Ellipsometry: Applications from Ultraviolet to Infrared", Hilfiker et al., J. Vac. Sci. Tecnol. A, (Jul/Aug. 2003).

"Atomic Scale Characterization of Semiconductors by In-Situ Real Time Spectroscopic Ellipsometry", Boher et al., Thin Solid Films 318 (1998).

"Optical Characterization in the Vacuum Ultraviolet with Variable Angle Spectroscopic Ellipsometry: 157nm and below", Hilfiker et al., Proc. SPIE vol. 3998 (2000).

"Feasibility and Applicability of Integrated Metrology Using Spectroscopic Ellipsometry in a Cluster Tool", Boher et al., SPIE vol. 4449, (2001).

"Characterization of Wide Bandgap Thin Film Growth Using UV-Extended Real Time Spectroscopic Ellipsometry Applications to Cubic Boron Nitride", Zapien et al., J. of Wide Bandgap Materials, vol. 9, No. 3 (Jan. 2002).

"Automated Rotating Element Ellipsometers: Calibration, Operation, and Real-Time Applications", Collins, Rev. Sci. Instrum. 61 (8) (Aug. 1990).

"Waveform Analysis With Optical Multichannel Detectors: Applications for Rapid-Scan Spectroscopic Ellipsometers", An et al., Rev. Sci. Instrum. 62(8), (Aug. 1991); and.

"Multichannel Ellipsometer for Real Time Spectroscopy of Thin Film Deposition for 1.5 to 6.5 eV", Zapien et al., Rev. Sci. Instrum, vol. 71, No. 9, (Sep. 1991).

* cited by examiner

ELLIPSOMETER OR POLARIMETER AND THE LIKE SYSTEM WITH MULTIPLE DETECTOR ELEMENT DETECTOR IN ENVIRONMENTAL CONTROL CHAMBER INCLUDING SECURE SAMPLE ACCESS

This application is a CIP of application Ser. No. 10/699,540 filed Nov. 1, 2003, Now U.S. Pat. No. 7,158,231 and therevia Claims benefit of Provisional 60/473,615 Filed May 28, 2003. This application also Claims benefit of Provisional Application Ser. No. 60/512,462 Filed Oct. 17, 2003.

TECHNICAL FIELD

The disclosed invention relates to ellipsometer or polarimeter and the like systems, and more particularly is an ellipsometer or polarimeter or the like system comprising a spectroscopic source of wavelengths and a detector with multiple detector elements, said system being at least partially present in an environmental control chamber, and preferably providing secure sample entry.

BACKGROUND

It is known to place ellipsometers and polarimeters and the like into environmental chambers where wavelengths which are absorbed by oxygen and water vapor and the like are utilized. However, all known system which do so presently are monochromater based. That is data is taken at a sequence of single wavelengths. Said approach is slow. Further, a recent PCT Published Application by Beaglehole, WO 2004/070363 A1, (PCT/NZ2004/000009), describes the positioning of a sample to be subjected to investigation using electromagnetic radiation be present in a sealed container which prevents contamination thereof during storage and sample analysis. A semicircular window through which electromagnetic radiation can be entered at any of many Angles-of-Incidence radially along a perpendicular to the surface of said semicircular window is also described.

Continuing, as general background, it is noted that Ellipsometry is a well known means by which to monitor samples. In brief, a polarized beam of electromagnetic radiation of one or more wavelengths is caused to impinge upon a sample, along one or more angles of incidence and then interact with a sample. Beams of electromagnetic radiation can be considered as comprised of two orthogonal components, (ie. "P" and "S"), where "P" identifies a plane which contains both an incident beam of electromagnetic radiation, and a normal to an investigated surface of a sample, being investigated, and where "S" identifies a plane perpendicular to the "P" plane and parallel to said surface of said sample. A change in polarization state in a polarized beam of electromagnetic radiation caused by said interaction with a sample, is representative of properties of said sample. (Note Polarization State basically refers to a magnitude of a ratio of orthogonal component magnitudes in a polarized beam of electromagnetic radiation, and a phase angle therebetween.) Generally two well known angles, (PSI and DELTA), which characterize a sample, at a given Angle-of-Incidence, are determined by analysis of data which represents change in polarization state. Additional sample identifying information is often also obtained by application of ellipsometry, including layer thicknesses, (including thicknesses for multilayers), optical thicknesses, sample temperature, refractive indicies and extinction coefficients, index grading, sample composition, surface roughness, alloy and/or void fraction, parameter dispersal and spectral dependencies on wavelength, vertical and lateral inhomogenieties etc.

Continuing, Ellipsometer Systems generally include a source of a beam of electromagnetic radiation, a Polarizer means, which serves to impose a linear state of polarization on a beam of electromagnetic radiation, a Stage for supporting a sample, and an Analyzer means which serves to select a polarization state in a beam of electromagnetic radiation after it has interacted with a sample, and pass it to a Detector System for analysis therein. As well, one or more Compensator(s) can be present and serve to affect a phase angle change between orthogonal components of a polarized beam of electromagnetic radiation.

It is noted that Spectroscopic Ellipsometer Systems utilize a Source which simultaneously provides a plurality of Wavelengths, which Source can be termed a "Broadband" Source of Electromagnetic radiation.

A number of types of ellipsometer systems exist, such as those which include rotating elements and those which include modulation elements. Those including rotating elements include Rotating Polarizer (RP), Rotating Analyzer (RA) and Rotating Compensator (RC). The presently disclosed invention can comprise a Rotating Compensator Ellipsometer System. It is noted that Rotating Compensator Ellipsometer Systems do not demonstrate "Dead-Spots" where obtaining data is difficult. They can read PSI and DELTA of a Sample over a full Range of Degrees with the only limitation being that if PSI becomes essentially zero (0.0), one can't then determine DELTA as there is not sufficient PSI Polar Vector Length to form the angle between the PSI Vector and an "X" axis. In comparison, Rotating Analyzer and Rotating Polarizer Ellipsometers have "Dead Spots" at DELTA's near 0.0 or 180 Degrees and Modulation Element Ellipsometers also have "Dead Spots" at PSI near 45 Degrees. The utility of Rotating Compensator Ellipsometer Systems should then be apparent. Another benefit provided by fixed Polarizer (P) and Analyzer (A) positions is that polarization state sensitivity to input and output optics during data acquisition is essentially non-existent. This enables relatively easy use of optic fibers, mirrors, lenses etc. for input/output.

A Search for relevant Patents was conducted. Most important is a Patent to Johs et al., U.S. Pat. No. 5,872,630, from which the present Application is derived as a CIP via intervening CIP Applications. Said 630 Patent describes:

A spectroscopic rotating compensator sample investigation system comprising a source of a polychromatic beam of electromagnetic radiation, a polarizer, a stage for supporting a sample, an analyzer, a dispersive optics and at least one detector system which contains a multiplicity of detector elements, said spectroscopic rotating compensator sample investigation system further comprising at least one compensator(s) positioned at a location selected from the group consisting of:
before said stage for supporting a sample;
after said stage for supporting a sample; and
both before and after said stage for supporting a sample;

such that when said spectroscopic rotating compensator sample investigation system is used to investigate a sample present on said stage for supporting a sample, said analyzer and polarizer are maintained essentially fixed in position and at least one of said at least one compensator(s) is caused to continuously rotate while a polychromatic beam of electromagnetic radiation produced by said source of a polychromatic beam of electromagnetic radiation is caused to pass through said polarizer and said compensator(s), said polychromatic beam of electromagnetic radiation being also caused to interact with said sample, pass through said analyzer and interact with said dispersive optics such that a multiplicity of essentially single wavelengths are caused to simultaneously enter a corresponding multiplicity of detector elements in said at least one detector system.

Said 630 Patent also, amongst other disclosure, describes a Mathematical Regression based Calibration procedure which makes possible the use of essentially any compensator regardless of non-achromatic characteristics.

Another Patent to Johs, from which the 630 Patent was Continued-in Part, is U.S. Pat. No. 5,666,201, filed Sep. 20, 1995. The focus in said 201 Patent comprises a detector arrangement in which multiple orders of a dispersed beam of electromagnetic radiation are intercepted by multiple detector systems. However, claim 8 in the 201 Patent, in combination with a viewing the Drawings therein, provide conception of the Spectroscopic Rotating Compensator Ellipsometer, as Claimed in claim 1 of the JAW 630 Patent and, in fact, the 630 Patent issued in view of a Terminal Disclaimer based upon the 201 Patent. A CIP of the 630 Patent, is U.S. Pat. No. 6,353,477 to Johs et al. which describes prefered multiple element compensators.

Also disclosed is U.S. Pat. No. 5,706,212, Issued Jan. 6, 1998, and Filed Mar. 20, 1996 for an Infrared Ellipsometer System Regression based Calibration Procedure. Said 212 Patent describes use of an Substantially Achromatic Rotating Compensator and application of Mathematical Regression in a Calibration procedure which evaluates calibration parameters in both rotating and stationary components. The 212 Patent describes that 2 OMEGA and 4 OMEGA associated terms are generated by a detector of a signal which passes through a compensator caused to rotate at a rate of OMEGA. Said 630 Patent was Continued-in-Part therefrom, as is the present Application via an intervening Patent Application. It is noted that the 212 Patent Application was filed four months prior to the earliest priority Patent Application, of Aspnes et al. Patents, (ie. U.S. Pat. Nos. 6,320,657 B1, 6,134,012, 5,973,787 and 5,877,859), the later of which was Filed on Jul. 24, 1996.

Relevant Patents to Aspnes et al. are U.S. Pat. Nos. 6,320,657 B1, 6,134,012, 5,973,787 and 5,877,859. These Patents describe a Broadband Spectroscopic Rotating Compensator Ellipsometer System wherein the Utility is found in the use of a "substantially Non-Achromatic" compensator, (see claim 1 in the 657 Patent), and selecting a Wavelength Range and Compensator so that "an effective phase retardation value is induced covering at least from 90 degrees to 180 degrees", (012 Patent), over a range of wavelengths of at least 200-800 nm. The 787 and 859 recite that at least one wavelength in said wavelength Range has a retardation imposed of between 135 and 225 Degrees, and another wavelength in the wavelength Range has a retardation imposed which is outside that retardation Range. The Utility of the Therma-wave Patents derives from the identified conditions being met so that at least one of a 2 OMEGA and a 4 OMEGA coefficient provided by a detector provides usable information at a wavelength, even when said coefficient does not provide usable information at other wavelengths. Again, the identified Aspnes et al. Patents recite directly, or describe the presence of a "substantially-non-Achromatic" compensator, while, it is noted at this point, the invention disclosed in this application utilizes what are properly termed substantially-achromatic or Psuedo-Achromatic compensators. It is further noted that the U.S. Pat. No. 5,716,212, from which this application Continues-in-Part, was filed prior to Jul. 24, 1976 filing date of the 859 Aspnes et al. priority Patent Application. The disclosed invention then has Priority to simultaneous use of 2 OMEGA and 4 OMEGA signals provided from a detector in a spectroscopic rotating compensator ellipsometer system which utilizes "Other-Than-Substantially Non-Achromatic" Compensators, namely "Substantially-Achromatic" or "Pseudo-Achromatic" Compensators, to characterize samples, emphasis added.

Two Patents which identify systems which utilize Polychromatic light in investigation of samples, U.S. Pat. Nos. 5,596,406 and 4,668,086 to Rosencwaig et al. and Redner, respectively, were also identified.

Also identified is a Patent to Woollam et al, U.S. Pat. No. 5,373,359 as it describes a Rotating Analyzer Ellipsometer System which utilizes white light. Patents continued from the 359 Woollam et al. Patent are, U.S. Pat. Nos. 5,504,582 to Johs et al. and 5,521,706 to Green et al. Said 582 Johs et al. and 706 Green et al. Patents describe use of polychromatic light in a Rotating Analyzer Ellipsometer System.

A Patent to Johs et al., No. 6,034,777 describes application of ellipsometry in an evacuated chamber comprising windows.

A Patent to Johs, U.S. Pat. No. 5,929,995 is disclosed as it describes application of ellipsometry in an evacuated chamber comprising windows.

A Patent to Bernoux et al., U.S. Pat. No. 5,329,357 is identified as it describes the use of optical fibers as input and output means in an ellipsometer system.

A Patent to Burns et al., U.S. Pat. No. 4,875,773 is disclosed as it describes an Optical System for a Multidetector Array Spectrograph.

A Patent to Freeouf, No. 6,414,302 is disclosed as it describes a High Photon Energy, (up through 10eV), Range Reflected Light Characterization System.

A Patent to Aspnes et al., No. 5,091,320 is disclosed as it describes application of ellipsometry with an evacuated chamber.

A Patent to Hartley, No. 4,770,895 is disclosed as it describes application of ellipsometry with an evacuated chamber.

A Published Patent Application by McAninch, No, 2002/0149774 A1 is disclosed as it describes purging a measurement region near a substrate in a metrology tool.

A J. A. Woollam CO. Flyer titled VUV-VASE (Registered Trademark), is disclosed as it describes a monochromater based rotating analyzer ellipsomete system in a purged chamber.

A Patent to Ivarsson, U.S. Pat. No. 6,493,097 is disclosed as it describes a Detector Array in an analytical instrument using electromagnetic radiation.

A Patent to Azzam, U.S. Pat. No. 5,337,146 is disclosed as it describes a spectrophotometer comprising a linear array detector.

A Patent to Wilkins et al., U.S. Pat. No. 6,031,619 describes an imaging spectrometer with a CCD Matrix or Row detector.

A Patent to Imai et al., U.S. Pat. No. 5,818,596 is disclosed as it describes use of purging gas to prevent contaminants on samples, but does not disclose ellipsometry or a multiple detector element detector array.

A Published Patent Application by McAninch, No, 2002/0149774 A1 is disclosed as it describes purging a measurement region near a substrate in a metrology tool.

A Published Patent Application by Wang et al., No. 2003/0071996 A1 is disclosed as it involves purging of the environment of one beam in a system involving two beams.

A Published Patent Application by Eckert et al., No. US 2003/0150997 A1 is disclosed as it describes use of VUV wavelengths and purging.

Regarding Articles,

An Article titled "A New Purged UV Spectroscopic Ellipsometer to Characterize Thin Films and Multilayers at 157 nm", Boher et al., Proc. SPIE, Vol. 3998, (June 2000) is disclosed as it describes a UV Spectroscopic Ellipsometer in combination with Purging.

A presentation titled "Characterisation of Thin Films and Multilayers in the VUV Wavelength Range Using Spectroscopic Ellipsometry and Spectroscopic Photometry", Boher et al., 157 nm Symposium, May 2000) is disclosed as it describes a UV Spectroscopic Ellipsometer.

A paper titled "Progress in Spectroscopic Ellipsometry: Applications from Ultraviolet to Infrared", Hilfiker et al., J. Vac. Sci. Technol. A, (July/August 2003) is disclosed as it discusses use of broadband wavelengths.

A paper titled "Atomic Scale Characterization of Semiconductors by In-Situ Real Time Spectroscopic Ellipsometry", Boher et al., Thin Solid Flims 318 (1998) is disclosed as it mentions multichannel detectors.

A paper titled "Optical Characterization in the Vacuum Ultraviolet with Variable Angle Spectroscopic Ellipsometry: 157 nm and below", Hilfiker et al., Proc. SPIE Vol. 3998 (2000) is disclosed as it describes use of the J. A. Woollam CO. VUV-VASE which is a monochromater based purged system.

A paper titled "Feasibility and Applicability of Integrated Metrology Using Spectroscopic Ellipsometry in a Cluster Tool", Boher et al., SPIE Vol. 4449, (2001) is disclosed as it describes a multichannelellipsometer applied outside an environmental chamber. This application required electromagnetic radiation to pass through windows to reach a sample.

Four papers authored or co-authored by Collins, which describe use of multichannels and rotating element ellipsometers, including rotating compensator, but not in an environmental chamber are:

"Characterization of Wide Bandgap Thin Film Growth Using UV-Extended Real Time Spectroscopic Ellipsometry Applications to Cubic Boron Nitride", Zapien et al., J. of Wide Bandgap Materials, Vol 9, No. 3 (January 2002);

"Automated Rotating Element Ellipsometers: Calibration, Operation, and Real-Time Applications", Collins, Rev. Sci. Instrum. 61 (8) (August 1990);

"Waveform Analysis With Optical Multichannel Detectors: Applications for Rapid-Scan Spectroscopic Ellipsometers", An et al., Rev. Sci. Instrum. 62(8), (August 1991); and "Multichannel Ellipsometer for Real Time Spectroscopy of Thin Film Deposition for 1.5 to 6.5 eV", Zapien et al., Rev. Sci. Instrum. Vol. 71, No. 9, (September 1991).

A book by Azzam and Bashara titled "Ellipsometry and Polarized light" North-Holland, 1977 is disclosed and incorporated herein by reference for general theory.

As well, identified for authority regarding regression, is a book titled Numerical Recipes in "C", 1988, Cambridge University Press.

While it is known to place ellipsometer systems outside environmental control chambers which require entering an electromagnetic beam through window, no prior art teaches a spectroscopic ellipsometer of any type which comprises a Detector system comprised of a multiplicity of detector elements, which detector elements simultaneously detect a multiplicity of wavelengths, said spectroscopic ellipsometer being contained within an environmental chamber, particularly when combined with the presence of a secured sample entry means.

DISCLOSURE OF THE INVENTION

The disclosed invention comprises a spectroscopic ellipsometer or polarimeter system comprising a source of a polychromatic beam of electromagnetic radiation, a polarizer, a stage for supporting a sample, an analyzer, a dispersive optics and at least one detector system which comprises a multiplicity of detector elements arranged in a selection from the group consisting of:
  one-dimensional; and
  multi-dimensional;

array. When said spectroscopic ellipsometer or polarimeter is used to investigate a sample present on said stage for supporting a sample, a polychromatic beam of electromagnetic radiation produced by said source of a polychromatic beam of electromagnetic radiation is caused to pass through said polarizer, interact with a sample on said stage for supporting a sample, pass through said analyzer and interact with said dispersive optics such that a multiplicity of essentially single wavelengths are caused to simultaneously enter a corresponding multiplicity of detector elements in said at least one detector system. Said spectroscopic ellipsometer or polarimeter system further comprises an environmental control chamber in which the spectroscopic ellipsometer or polarimeter is contained, said environmental control chamber being characterized by a selection from the group consisting of:

it comprises one chamber region in which is present a polarization state generator comprising components prior to said sample, said sample, and a polarization state detector comprising components after said sample;

it comprises three chamber regions, in one of which is present a polarization state generator comprising all components prior to said sample, in the second of which is present the sample and in the third of which is present a polarization state detector comprising components after said sample;

it comprises two chamber regions, in one of which is present a polarization state generator comprising components prior to said sample and said sample, and in the second of which is present a polarization state detector comprising components after said sample;

it comprises two chamber regions, in one of which is present a polarization state generator comprising components prior to said sample, and in the second of which is present said sample and a polarization state detector comprising components after said sample;

and in a prefered embodiment, said chamber in which is present the sample further comprises means for entering said substantially sealed container thereinto without substantially affecting the environment therewithin.

The multiplicity of detector elements can be arranged in a one-dimensional or multi-dimensional (eg. two), array.

The disclosed invention can comprise, within an environmental control chamber, a spectroscopic rotating compensator sample investigation system comprising a source of polychromatic beam of electromagnetic radiation, a polarizer, a stage for supporting a sample, an analyzer, a dispersive optics and at least one detector system which contains a multiplicity of detector elements, said spectroscopic rotating compensator sample investigation system further comprising at least one compensator(s) positioned at a location selected from the group consisting of:

before said stage for supporting a sample;
after said stage for supporting a sample; and
both before and after said stage for supporting a sample;

When said spectroscopic rotating compensator sample investigation system is used to investigate a sample present on said stage for supporting a sample, said analyzer and polarizer are maintained essentially fixed in position and at least one of said at least one compensator(s) is caused to continuously rotate while a polychromatic beam of electromagnetic radiation produced by said source of a polychromatic beam of electromagnetic radiation is caused to pass through said polarizer and said at least one compensator(s). Said polychromatic beam of electromagnetic radiation is then caused to interact with a sample on said stage for supporting a sample, pass through said analyzer interact with said dispersive optics such that a multiplicity of essentially single wavelengths are caused to simultaneously enter a corresponding multiplicity of detector elements in said at least one detector system. The prefered detector dispersive optics and detector elements can be contained in an off-the-shelf diode array spectrometer system, with an operational wavelength range selected from the group consisting of:

300-1150 nm;
190-730 nm;
190-400 nm; and
900-2400 nm;

and optionally the detector which demonstrates a quantum efficiency of at least greater than forty (40%) percent.

The dispersive optics is preferably a diffraction grating characterized by a selection from the group consisting of:

a "lined";
a "blazed"; and
a "holographic" geometry;

said lined geometry consisting essentially of symmetrical alternating lines with depressions therebetween, and said blazed geometry consisting of alternating ramp shaped lines with depressions therebetween, and said holographic geometry consisting of continuous cosine shaped lines and depressions. However, said dispersive optics can comprise a prism.

At this point it is beneficial to recite a method of quickly simultaneously taking data at a multiplicity of wavelengths including wavelengths which are, and are not absorbed by environmental components. Said method comprises the steps of:

a) providing a spectroscopic ellipsometer or polarimeter system comprising a source of a polychromatic beam of electromagnetic radiation, a polarizer, a stage for supporting a sample, an analyzer, a dispersive optics and at least one detector system which comprises a multiplicity of detector elements;

such that when said spectroscopic ellipsometer or polarimeter is used to investigate a sample present on said stage for supporting a sample, a polychromatic beam of electromagnetic radiation produced by said source of a polychromatic beam of electromagnetic radiation is caused to pass through said polarizer and interact with a sample on said stage for supporting a sample, then pass through said analyzer, and interact with said dispersive optics such that a multiplicity of essentially single wavelengths are caused to simultaneously enter a corresponding multiplicity of detector elements in said at least one detector system;

said spectroscopic ellipsometer or polarimeter system further comprising an environmental control chamber in which the spectroscopic ellipsometer or polarimeter is contained, said environmental control chamber being characterized by a selection from the group consisting of:

it comprises one chamber region in which is present a polarization state generator comprising components prior to said sample, said sample, and a polarization state detector comprising components after said sample;

it comprises three chamber regions, in one of which is present a polarization state generator comprising all components prior to said sample, in the second of which is present the sample and in the third of which is present a polarization state detector comprising components after said sample;

it comprises two chamber regions, in one of which is present a polarization state generator comprising components prior to said sample and said sample, and in the second of which is present a polarization state detector comprising components after said sample;

it comprises two chamber regions, in one of which is present a polarization state generator comprising components prior to said sample, and in the second of which is present said sample and a polarization state detector comprising components after said sample and said sample;

b) placing a sample on said stage for supporting a sample and at least partially purging or evacuating said environmental control chamber;

c) causing said source of polychromatic beam of electromagnetic radiation to provide a polychromatic beam of electromagnetic radiation and causing said beam to interact with said sample on said stage for supporting a sample, and interact with said dispersive optics such that a multiplicity of essentially single wavelengths are caused to simultaneously enter a corresponding multiplicity of detector elements in said at least one detector system.

Said method of quickly simultaneously taking data at a multiplicity of wavelengths can involve providing at least one detector system can comprise applying a multiplicity of detector elements in a one-dimensional array or in a multi-dimensional array. No known system provides an ellipsometer or polarimeter and the like system with a multi-detector element detector in an environmental control chamber so as to enable simultaneously obtaining data at a plurality of wavelengths, at least some of which are absorbed by oxygen or water vapor and the like.

The disclosed invention also comprises providing a sample in a container which is substantially sealed during storage, but which can be opened once placed into a system which provides a source and detector of electromagnetic radiation which can provide and detect a beam of electromagnetic radiation which is caused to interact with said sample. The present invention enables exposing the sample directly to the environment inside an evacuated or purged contained volume once the sample in its container are entered into said evacuated or purged contained volume, but which enables securing said sample against the external environment when it is removed therefrom.

Realization of the presently disclosed invention can involve a sliding or hinged door on the sample container, but any functional system is within the scope thereof.

The disclosed invention is then further a system comprising:

a) an environmental control chamber comprising means for evacuating or purging an internal volume thereof and means for causing a beam of electromagnetic radiation to interact with a sample placed therewithin;

b) a sample in a substantially sealed container, said substantially sealed container having means for opening direct access to said sample;

c) said environmental control chamber comprising means for entering said substantially sealed container thereinto without substantially affecting the environment therewithin.

A disclosed invention method of investigating a sample comprises the steps of:

a) providing a system comprising:

an environmental control chamber comprising means for evacuating or purging an internal volume thereof and means for causing a beam of electromagnetic radiation to interact with a sample placed therewithin;

a sample in a substantially sealed container, said substantially sealed container having means for opening direct access to said sample;

said environmental control chamber comprising means for entering said substantially sealed container thereinto without substantially affecting the environment therewithin;

b) operating said means for evacuating or purging an internal volume to effect a desired environment inside said environmental control chamber;

c) utilizing said means for entering said substantially sealed container into said environmental control chamber without substantially affecting the environment therewithin, to enter said sample in said substantially sealed container thereinto;

d) operating said means for opening direct access to said sample to open direct access to said sample within said environmental control chamber;

e) causing said means for causing a beam of electromagnetic radiation to interact with a sample placed therewithin to cause a beam of electromagnetic radiation to interact with said sample; and f) detecting said electromagnetic which interacts with said sample after it interacts with said sample.

Said Method can Further Comprise g) operating said means for opening direct access to said sample to close direct access to said sample within said environmental control chamber;

h) utilizing said means for entering said substantially sealed container into said environmental control chamber without substantially affecting the environment therewithin, to remove said sample in said substantially sealed container from said environmental control chamber without substantially affecting the environment therewithin.

The disclosed invention will be better understood by a reading of the Detailed description Section, in combination with the Drawings.

SUMMARY OF THE INVENTION

It is therefore a purpose and/or objective of the disclosed invention to teach a spectrophotometer, ellipsometer, polarimeter or the like system which comprises a spectroscopic source of electromagnetic radiation, and a dispersive optics and multi-element detector for simultaneous monitoring a multiplicity of wavelengths simultaneously, in an environmental control chamber.

It is another purpose and/or objective of the disclosed invention to teach a spectrophotometer, ellipsometer, polarimeter or the like system in an environmental control chamber which comprises means for entering a sample in thereto without substantially affecting the environment therein.

It is yet another purpose and/or objective of the disclosed invention to teach a Sample in a substantially sealed Sample Container, and a spectrophotometer, ellipsometer, polarimeter or the like system in an environmental control chamber which comprises an entry chamber for use in entering and removing said substantially sealed Sample Container without substantially affecting the environment in said environmental control chamber.

Other purposes and/or objectives will be apparent from a reading of the Specification and Claims.

DETAILED DESCRIPTION

Figures 1A, 1C, 1D:
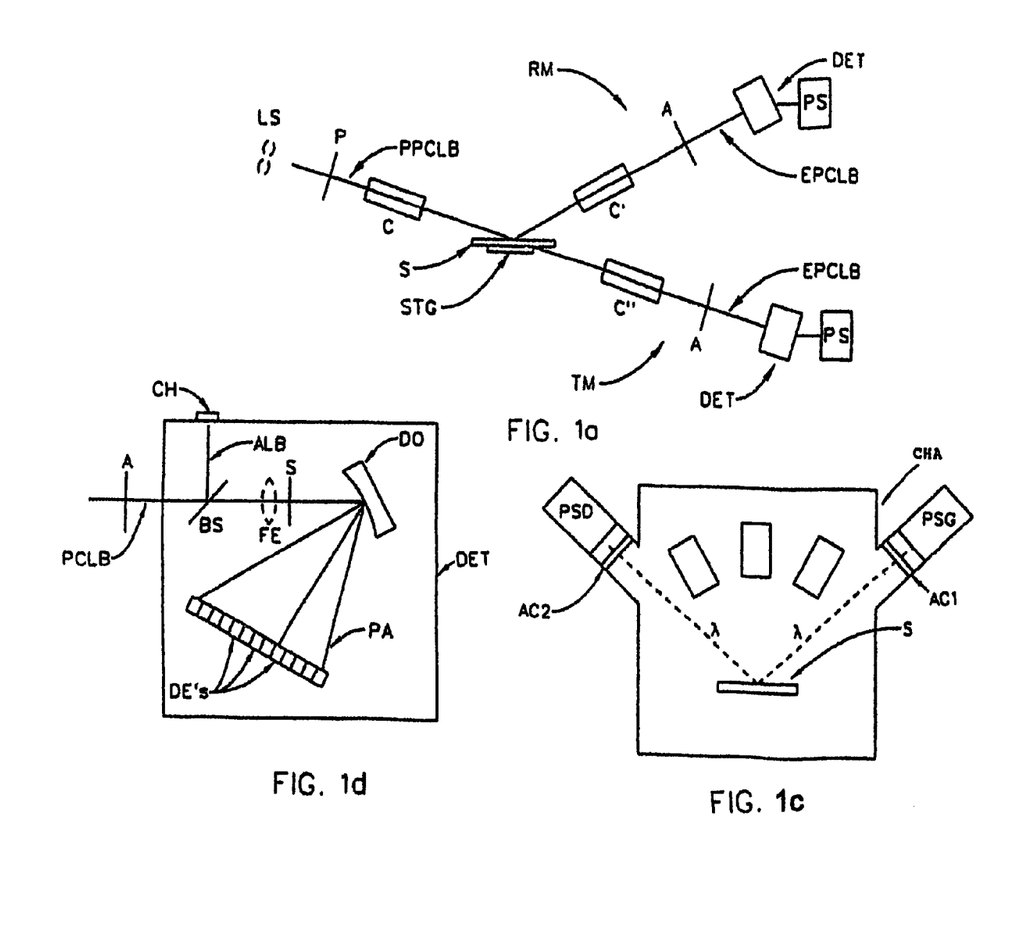
FIG. 1a shows the basic components of Reflectance and Transmission Mode Sample Investigation Systems.
FIG. 1c demonstrates a multi-chamber environmental control Chamber into which systems such as demonstrated in FIGS. 1a and 1b systems can be present.
FIG. 1d provides insight to a dispersive optics and detector arrangement.

Referring now to FIG. 1a, there is demonstrated a Material System Investigation System, (ie. a Spectroscopic Ellipsometer System), with provision to investigate a Sample (S) in either a Reflection Mode (RM) or a Transmission Mode (TM). It is to be noted that said Sample investigation System is generally comprised of a Source of a Polychromatic Beam of Electromagnetic Radiation (LS), (ie. a Broadband electromagnetic radiation source), a Polarizer Means (P), a Sample, supporting Stage (STG), an Analyzer-Means (A) and a Detector Elements (DE's) containing Photo Array Detector Means System (DET). Also note, however, that FIG. 1a shows Reflection Mode System Compensator(s) Means (C) and (C') and Transmission Mode System Compensator(s) Means (C) and (C") as present. It is to be understood that a Compensator Means can be placed ahead of, and/or after a Material System (S) supporting Stage (STG) in either a Reflection Mode or Transmission Mode System. That is only Compensator Means (C) or (C') or both Compensator Means (C) and (C') can be present in a Reflection Mode System (RM), and only Compensator Means (C) or (C") or both Compensator Means (C) and (C") can be simultaneously present in the Transmission Mode System (TM). FIG. 1a also shows the presence of a Processor (PS) for performing calculations that evaluate a sample based on the Detector (DET) intensity output signal.

The configuration in FIG. 1a could be operated as a Rotating Polarizer or Rotating Analyzer System. The disclosed Rotating Compensator Sample Investigation System, however, in the preferred operational mode, essentially fixes the Polarizer Means (P) and Analyzer Means (A) during Data Acquisition from a Sample (Sample) (S) which is placed upon the Sample supporting Stage (STG), and causes at least one present Compensator Means ((C), and/or (C') or (C) and/or (C")), to Rotate during said Data Acquisition. This serves to effectively enter a continuously varying retardance between Orthogonal Components in a Polarization Beam of Electromagnetic Radiation exiting said Compensator Means which is caused to rotate. Where two (2) Compensator Means are present, one before (C) and one after ((C') or (C")) a Sample placed upon said Sample (S) supporting Stage (STG), only one, or both said Compensator Means can be caused to Rotate in use. If both Compensator Means are caused to rotate, both can be rotated at the same rotation speed, or different rotation speeds can be utilized. It is noted that the J. A. Woollam CO. Rotating Compensator Ellipsometer uses a "Stepper Motor" to cause Compensator rotation, and a common signal synchronizes both the Compensator and Detector. An alternative technique is to use a signal derived from the motor to synchronize the detector. It is further noted that fixing the Polarizer Means (P) and Analyzer Means (A) in use provides another benefit in that polarization state sensitivity to input and output optics during data acquisition is essentially non-existent. This allows use of Optic Fibers, Mirrors, Beam Splitters, Lenses etc. for input/output.

Figure 1B:
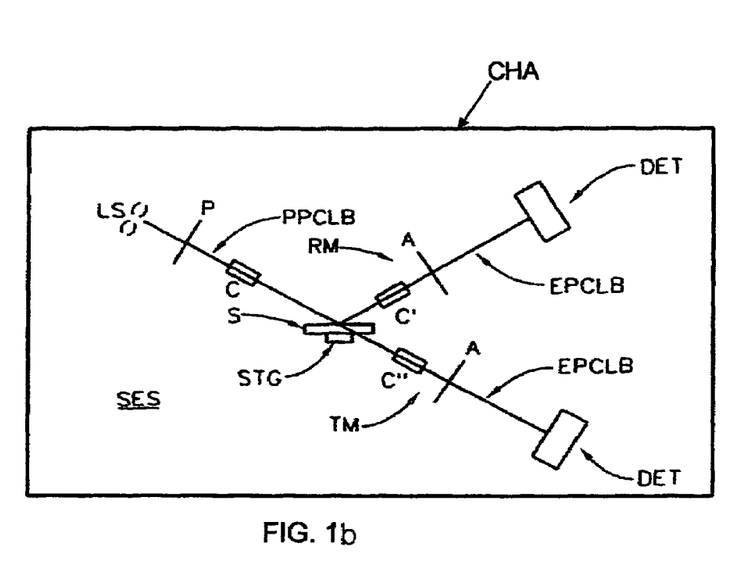
FIG. 1b demonstrates an entire ellipsometer or polarimeter in an environmental Chamber (CHA).

It is also mentioned that in the following it will be generally assumed that a Sample (S) under investigation by a Spectroscopic Rotating Compensator Sample Investigation System is positioned upon the Sample Supporting Stage (STG). This need not be the case, as is described in U.S. Pat. No. 5,706,087 wherein a Sample (Sample), (S) can be positioned in a Magneto-Optic System which is physically too large to be supported by said Sample Supporting Stage (STG), or in an environmental control chamber. Further, especially where Ultraviolet range wavelengths are utilized, the system of FIG. 1a or 1b can be placed into an evacuated or purged, (eg. by nitrogen or argon), Chamber to the end that UV absorbing Oxygen and Water Vapor are not present therewithin. The entire FIG. 1a or 1b system can be so encompassed within a said Chamber, or only the Sample (S) Stage portion thereof. The Chamber can be of multiple region construction. FIG. 1c shows a Chamber (CHA) which can be interpreted to contain one or multiple interior regions and FIG. 1d shows a one region environmental control chamber (CHA). For instance the FIG. 1a Pre-(S) Polarization State Generator (PSG) and Post-(S) Polarization State Detector (PSD) can be open to the region containing the Sample (S), or can be considered to be sequestered by (AC1) and (AC2) so that the internal environments available to each can be controlled to be are the same or different. More specifically, the environmental chamber can have a configuration characterized by a selection from the group consisting of:

it comprises at least one chamber region in which is present polarization state generator (PSG) comprising component(s) prior to said sample, said sample (S), and polarization state detector (PSD) comprising component(s) after said sample;

it comprises at least three chamber regions, in one of which is present polarization state generator (PSG) comprising component(s) prior to said sample (S), in the second of which is present the sample (S) and in the third of which is present polarization state detector (PSD) comprising component(s) after said sample (S);

it comprises at least two chamber regions, in one of which is present polarization state generator (PSG) comprising component(s) prior to said sample (S) and said sample (S), and in the second of which is present polarization state detector (PSD) comprising component(s) after said sample MS;

it comprises at least two chamber regions, in one of which is present polarization state generator comprising component(s) prior to said sample, and in the second of which is present polarization state detector comprising component(s) after said sample and said sample; and in a prefered embodiment, said chamber in which is present the sample further comprises means for entering said substantially sealed container thereinto without substantially affecting the environment therewithin.

The environment in any chamber region can be individually controlled, or the environment in all chamber regions can be similarly controlled. This includes allowing the chamber regions containing the polarization state generator (PSG) and the polarization state detector (PSD) to be in ambient with only a sample (S) under investigation being in a Controlled Environment (SES).

Figure 1E:
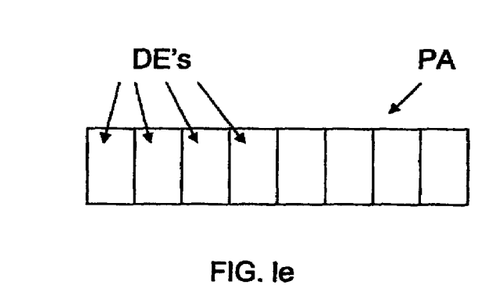
FIGS. 1e and 1f demonstrate one and multi-dimensional Detectors (DET) comprising a multiplicity of detector elements (DE's).
Figure 1F:
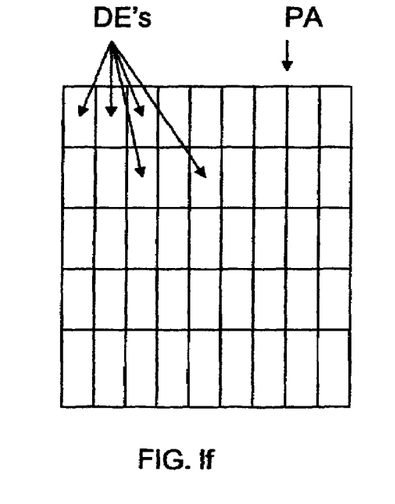
Figure 3:
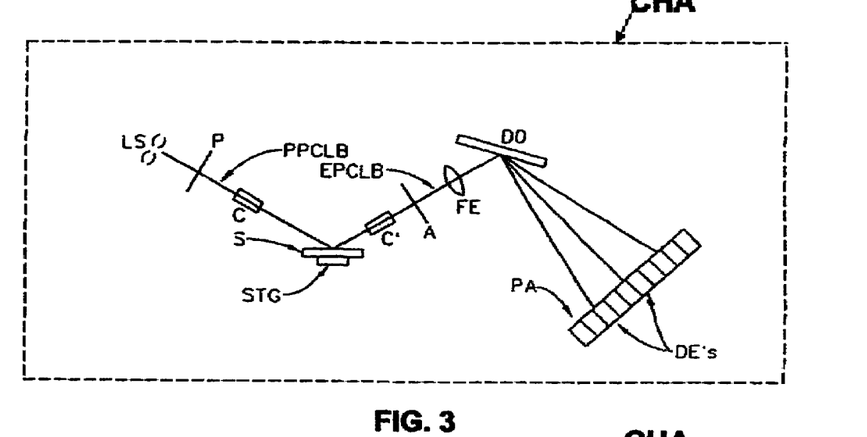
FIG. 3 shows a Reflectance Mode combination of components shown in FIGS. 1a and 1c.
Figure 4:
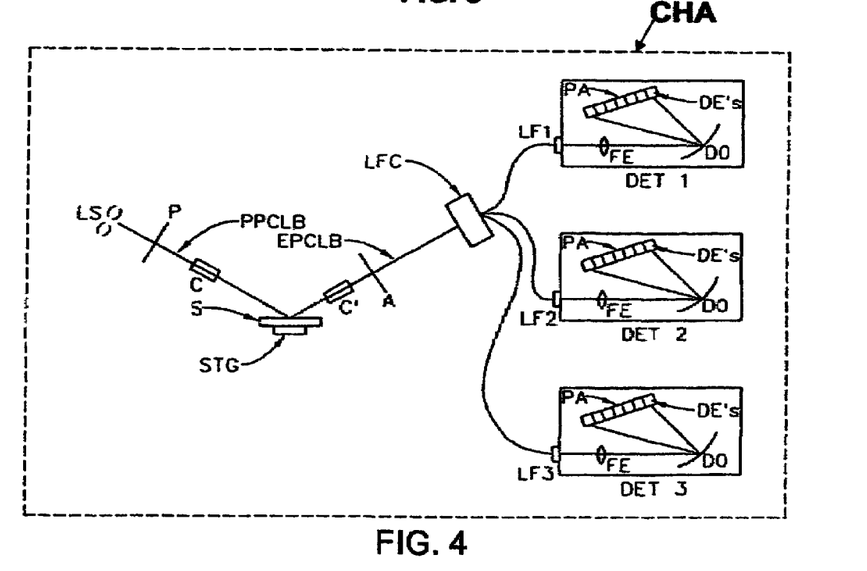
FIG. 4 shows a Reflectance Mode combination of components shown in FIGS. 1a and 1c in which three FIG. 1d Spectrographic Diode Array Spectrometer Systems are present and provided input via light fibers.
Figure 5:
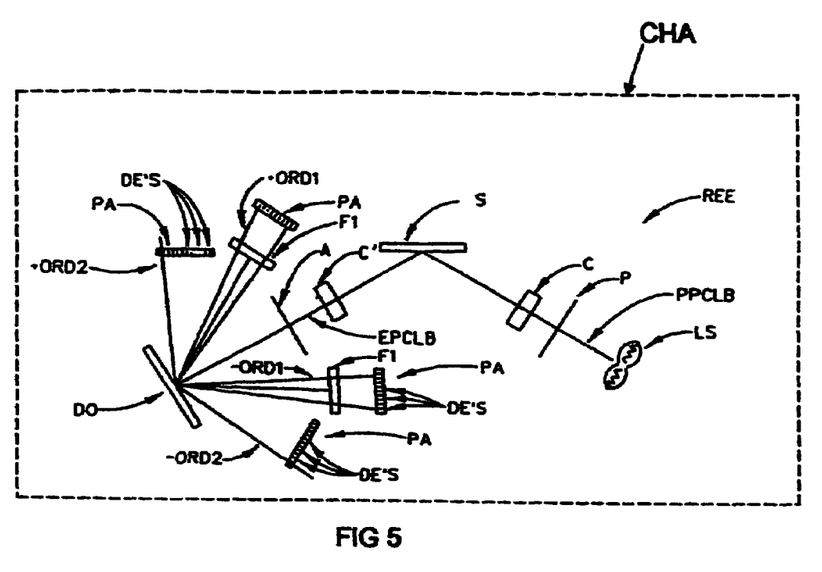
FIG. 5 shows a Reflectance Mode combination of components shown in FIGS. 1a and 1c in which Multiple Orders produced by a Dispersive Optics are intercepted by multiple Photo Arrays.

FIG. 1d demonstrates an entire ellipsometer or polarimeter in an Environmental Chamber (CHA). Shown in a Controlled Environment (SES), prior to a Stage (STG) with a Sample (S) present thereupon, are a Source of a Beam (PPCLB) of Electromagnetic Radiation (LS), a Polarizer, a Compensator (C). Also shown are Reflection (RM) and Transmission (TM) Mode sequences of Compensator (C") (C'''), Analyzer (A) and Detector (DET) into each of which is shown entering an Electromagnetic Beam (EPCLB). FIGS. 1e and 1f demonstrate that the Detector (DET) preferably comprises multiple Detector Element (DE's), as shown in FIGS. 3, 4 and 5a, (any of which can likewise be in an environmental chamber (CHA)). This can be of particular benefit where speed of data acquisition is important as it allows multiple wavelengths to be simultaneously detected. To the Inventor's knowledge, no existing system allows simultaneous detection of multiplicity of wavelengths in ranges which are absorbed by oxygen or H2O vapor etc., (eg. IR and UV-DUV-VUV).

Continuing, as alluded to, the disclosed invention utilizes a Broadband source of Polychromatic Electromagnetic Radiation (LS), and FIG. 1d shows that the Detector Elements (DE's) containing Detector System (DET) is, in the preferred embodiment, comprised of a Photo Array which consists of a number of Diode Elements (DE's), (any functionally equivalent, though structurally different, Detector Element (DE's) are to be considered equivalent for the purposes of Claim construction). In use a Dispersive Optics (DO) receives a Polychromatic Electromagnetic Beam (EPCLB) which has interacted with a Material System (S) and passed through said Analyzer Means (A), and diffracts said Polychromatic Electromagnetic Beam (EPCLB), such that each Photo Array (PA) Diode Element (DE) intercepts an Essentially Single Wavelength, (eg. a small band of wavelengths centered about a central single wavelength). Note that a Focusing Element (FE) is shown in a dashed line format to indicate that its presence is optional. The Focusing Element (FE), when present, serves to provide a focused Polychromatic Beam of Electromagnetic Waves at the input to said Detector Elements (DE's) containing Photo Array Detector System (DET), and the Detector System (DET) provides 2 and 4 signals developed by the Diode Elements (DE's) in a sequential output or a parallel output from the Diode Elements (DE's). It is emphasized that a preferred Detector Elements (DE's) containing Photo Array Detector System (DET) is an "Off-the-Shelf-System" which includes a Focusing Element (FE), and provides a self contained Dispersive Optics (DO) and Diode Element (DE) Array. The "Off-The-Shelf-System" of said preferred embodiment of the Rotating Compensator Sample Investigation System is a Zeiss Diode Array Spectrometer System identified by manufacturer numbers in the group: (MMS1 (300-1150 nm); UV/VIS MMS (190-730 nm); UV MMS (190-400 nm); AND IR MMS (900-2400 nm)). Said identified Zeiss systems provide a very compact system comprising a multiplicity of Detector Elements (DE's), and provide focusing via a Focusing Element (FE), Slit (S), and single concave holographic grating dispersive optics (DO), as generally represented by FIG. 1$d$. A Hamamatsu CCD Array Detector, (Series S7030/S7031), with a quantum efficiency of 40% or more has been successfully utilized.

Note that FIG. 1$d$ also shows the presence of a Beam Splitter (BS) and a Cross Hair containing Reticule (CHA) in the Detector Elements (DE's) containing Photo Array Detector System (DET). If the Beam Splitter (BS), the Dispersive Optics (DO), the Focusing Element (FE), the Detector Elements (DE's) containing Photo Array (PA), and the Cross Hair containing Reticule (CHA) are mounted so as to move as a rigid unit, then it should be appreciated that causing an Alignment Electromagnetic Radiation Beam (ALB) which reflects to said Cross Hair containing Reticule (CHA) to be present near a Cross Hair crossing point can effect good alignment of the Detector Elements (DE's) containing Photo Array Detector System (DET) with respect to an entering Polarized Beam of Electromagnetic Radiation (EPCLB). In practice such an arrangement has been found to work very well. It is further noted that the element identified as (CHA) could represent a Quadrature Photodetector and Automatic Alignment Means, or other functionally suitable system.

FIG. 2$a$ shows a Chamber (CHA), in which is present a sample (S) during use, comprising means for evacuating or purging (not shown), an internal volume thereof and means for causing a beam (LS) of electromagnetic radiation to interact with a Sample (S) placed therewithin. Said chamber also comprises means for entering said substantially sealed Sample Container (SC) thereinto without substantially affecting the environment therewithin. Note the function demonstrating presence of a demonstrative First and Second Double Door (D1) (D2) arrangement which allows opening First Door (D1) and entering a substantially sealed Sample Container (SC) (see FIGS. 2$b$ and 2$d$), while maintaining Second Door (D2) in a closed position. Once the substantially Sample Container (SC) is entered to Entry Chamber (ECH), First Door (D1) is closed and Second Door (D2) opened, thereby allowing the substantially sealed Sample Container (SC) to be entered to the Chamber (CHA). This progression allows entry of the substantially sealed Sample Container (SC) into the Chamber (CHA) without substantially contaminating the environment therein. Any means for such entry which is functionally equivalent is to be considered within the scope of the present invention. FIGS. 2$c$ and 2$d$ show the Sample in a substantially sealed Sample Container (SC). Note that FIG. 2$b$ shows a Lid (L) moving Motor (M) can be associated with the sealed Sample Container (SC), said Motor (M) being remotely controlled from outside the Chamber (CHA), when said Sample Container (SC) is inside thereof.

Figure 2A:
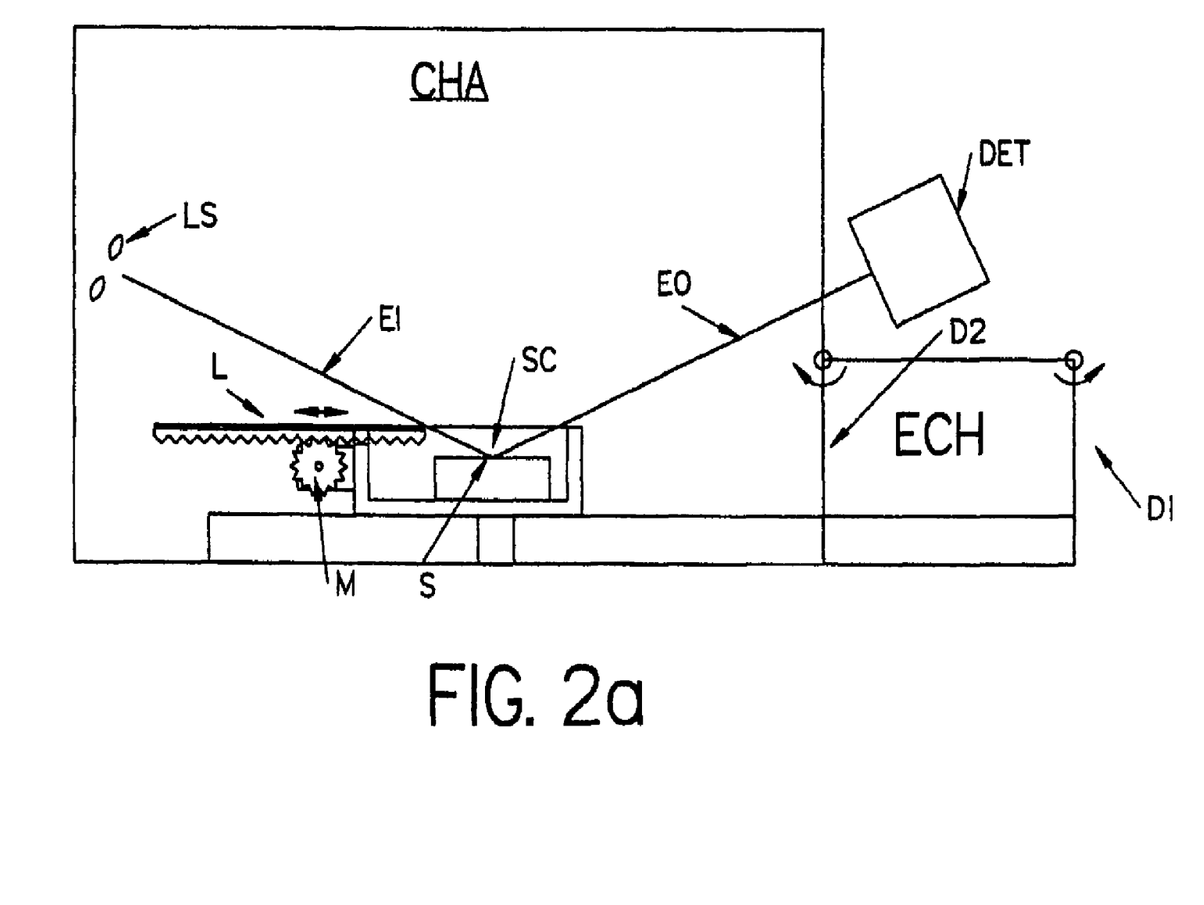
FIG. 2a shows an environmental Chamber (CHA) comprising means for evacuating or purging (not shown), an internal volume thereof and means for causing a beam (LS) of electromagnetic radiation to interact with a Sample (S) placed therewithin.

Once in place in Chamber (CHA), the Sample Container (SC) is opened so that Beam (EI) can interact with said Sample (S) and reflect therefrom as Beam (EO).

Figure 2B:
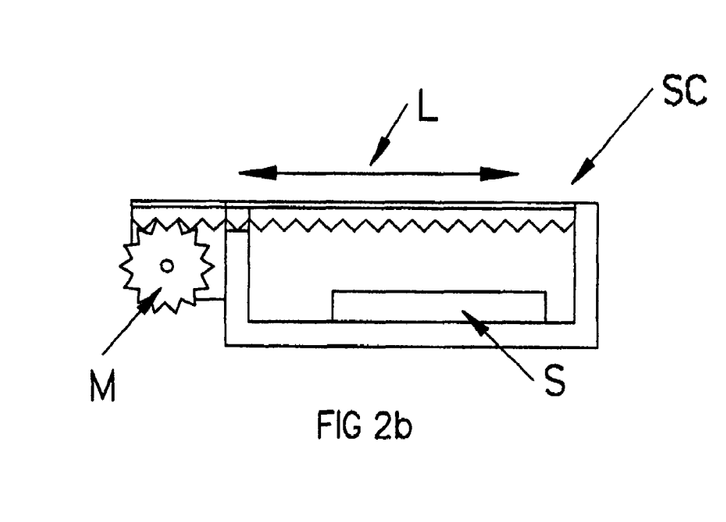
FIG. 2b shows a Lid (L) moving Motor (M) can be associated with the sealed Sample Container (SC).
Figure 2C:
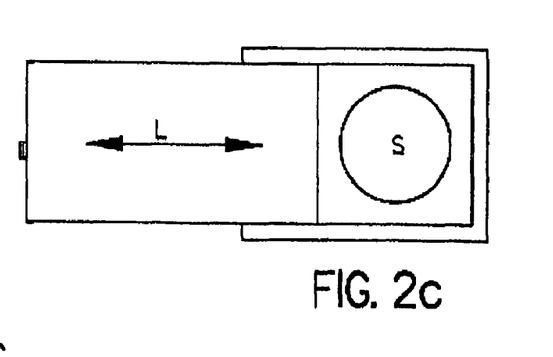
FIGS. 2c and 2d show the Sample in a substantially sealed Sample Container (SC).
Figure 2D:
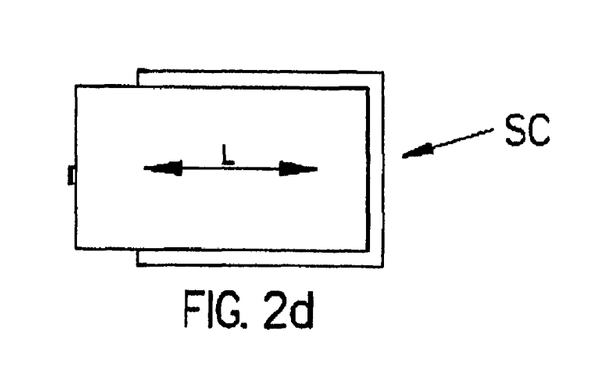

After investigation of the Sample (S), the substantially sealed Sample Container (SC) is again closed and removed from the Chamber (CHA), via the Entry Chamber (ECH), it is allowed to remain substantially sealed, thereby protecting the Sample (S) therewithin from contamination. It is noted that such removal would involve causing Lid (L) the assume the position shown in FIGS. 2$b$ and 2$d$, then opening the Second Door (D2), moving the Sample Container (SC) into the Entry Chamber (ECH), closing said Second Door (D2), then opening the First Door (D1) and completing removal of said Sample Container (SC) into the Entry Chamber (ECH).

It is noted that the environmental control Chamber (CHA) can be evacuated, purged or maintained at positive pressure. In any case, the present invention serves to protect the Sample (S) against contact with untoward atmospheric conditions.

Now, it is to be understood that the system of the Spectroscopic Rotating Compensator Sample Investigation System is basically found in a combination of components shown in FIGS. 1$a$, 1$b$, 1$c$ and 2, the basic result of said combination, for a Reflection Mode System, being shown in FIG. 3. That is, FIG. 3 shows a Spectroscopic Reflection Mode version of the Rotating Compensator Sample Investigation System shown in FIG. 1$a$, with the FIG. 2 Detector Elements (DE's) containing Photo Array Detector System (DET) shown present directly after the Analyzer (A).

FIG. 4 shows a Reflection Mode System configuration in which three (3) Detectors (Det 1), (Det 2) and (Det 3) are fed input by Fiber Optics (LF1), (LF2) and (LF3) present in a Fiber Optic Bundle exiting Fiber Optic Connector (LFC). Said Fiber Optic Connector (LFC) receives a Polarized Electromagnetic Beam (EPCLB) exiting the Analyzer (A). (Note that a FIG. 9$c$ at least Bifrucated Fiber Optic could be utilized). Said three (3) Detectors (Det 1), (Det 2) and (Det 3) can be previously disclosed Off-the-shelf Zeiss Diode Array Spectrometers, and can each comprise a Focusing Element (FE) in functional combination with a Dispersive Optics (DO) and a Diode Element (DE) containing Photo Array (PA).

FIG. 5 shows that the described system can cause a Polychromatic Beam of Polarized Electromagnetic Radiation (PPCLB) to, after interaction with a Sample (S), reflect therefrom. FIG. 5$a$ shows that the Reflected Polarized Beam of Electromagnetic Radiation (EPCLB), is caused to impinge upon a Dispersive Optics (DO), (eg. a Diffraction Grating), such that a plurality of Orders (+ORD2, +ORD1, −ORD1 and −ORD2) are produced. Each said Order is comprised of a spectrum of Wavelengths, and FIG. 5$a$ shows that Wavelengths in said Orders (+ORD2, +ORD1, −ORD1 and −ORD2) can be intercepted by Detector elements (DE's) in Photo Arrays (PA). Some embodiments of a Rotating Compensator Ellipsometer System utilize such a system. It is noted that the Dispersive Optics (DO) is typically rotatable so that the direction each Order of wavelengths generally proceeds from said Dispersive Optics (DO) is adjustable. Note that FIG. 5 also shows the presence of Filters (F1). It is noted that wavelengths for adjacent Orders overlap, and said Filters (F1) allow a user to pass only desired Wavelengths, as well as reduce background radiation entry to Photo Arrays (PA's). Typically a Focusing Element is not present in a FIG. 5 embodiment.

Analogically similar figures to those shown in FIGS. 2a, and 3-5, but oriented for use in a Transmission Mode are not shown, but should be understood as within the scope of the present invention implied by FIG. 1a. Further, while FIGS. 2a, and 3-5 comprise one Environmentally Controlled Chamber region, the present invention is not so limited and the Multiple Chamber embodiment shown in FIG. 1c is to be considered as also applicable to and represented by said FIGS. 3-5.

Having hereby disclosed the subject matter of the present invention, it should be obvious that many modifications, substitutions, and variations of the present invention are possible in view of the teachings. It is therefore to be understood that the invention may be practiced other than as specifically described, and should be limited in its breadth and scope only by the Claims.

We claim:

1. A system comprising:
   a) an environmental control chamber comprising means for evacuating or purging an internal volume thereof and means for causing a beam of electromagnetic radiation to interact with a sample placed therewithin;
   b) said sample being in a substantially sealed container, said substantially sealed container having means for opening direct access to said sample;
   c) said environmental control chamber comprising means for entering said substantially sealed container thereinto without substantially affecting the environment therewithin which comprises first and second doors, such that in use the first door is closed to secure the environmental control chamber and the second door is opened to allow entry of said sample in a substantially sealed container into said entry chamber, followed by said second door being closed and said first door being opened to allow entry of said sample in a substantially sealed container into said environmental control chamber, said procedure being reversed to remove said sample in a substantially sealed container from said environmental control chamber.

2. A system as in claim 1, in which said environmental control chamber is characterized by a selection from the group consisting of:
   it comprises one chamber region in which is present a polarization state generator comprising components prior to said sample, said sample, and a polarization state detector comprising components after said sample;
   it comprises three chamber regions, in one of which is present a polarization state generator comprising all components prior to said sample, in the second of which is present the sample and in the third of which is present a polarization state detector comprising components after said sample;
   it comprises two chamber regions, in one of which is present a polarization state generator comprising components prior to said sample and said sample, and in the second of which is present a polarization state detector comprising components after said sample;
   it comprises two chamber regions, in one of which is present a polarization state generator comprising components prior to said sample, and in the second of which is present said sample and a polarization state detector comprising components after said sample;
   wherein said chamber in which is present said sample in said substantially sealed container comprises said means for entering and removing said substantially sealed container without substantially affecting the environment therewithin.

3. A spectroscopic ellipsometer or polarimeter system comprising a source of a polychromatic beam of electromagnetic radiation, a polarizer, a stage for supporting a sample, an analyzer, a dispersive optics and at least one detector system which comprises a multiplicity of detector elements arranged in a selection from the group consisting of a:
   one-dimensional; and
   multi-dimensional;
array, such that when said spectroscopic ellipsometer or polarimeter is used to investigate a sample present on said stage for supporting a sample, a polychromatic beam of electromagnetic radiation produced by said source of a polychromatic beam of electromagnetic radiation is caused to pass through said polarizer, interact with a sample on said stage for supporting a sample, pass through said analyzer and interact with said dispersive optics such that a multiplicity of essentially single wavelengths are caused to simultaneously enter a corresponding multiplicity of detector elements in said at least one detector system;
said spectroscopic ellipsometer or polarimeter system further comprising an environmental control chamber in which the spectroscopic ellipsometer or polarimeter is contained, said environmental control chamber being characterized by a selection from the group consisting of:
   it comprises one chamber region in which is present a polarization state generator comprising components prior to said sample, said sample, and a polarization state detector comprising components after said sample;
   it comprises three chamber regions, in one of which is present a polarization state generator comprising components prior to said sample, in the second of which is present the sample and in the third of which is present a polarization state detector comprising components after said sample;
   it comprises two chamber regions, in one of which is present a polarization state generator comprising components prior to said sample and said sample, and in the second of which is present a polarization state detector comprising components after said sample;
   it comprises two chamber regions, in one of which is present a polarization state generator comprising components prior to said sample, and in the second of which is present said sample and a polarization state detector comprising components after said sample;
said chamber in which is present said sample further comprising means for entering and removing said sample without substantially affecting the environment therewithin which comprises first and second doors, such that in use the first door is closed to secure the chamber in which a sample is placed, and the second door is opened to allow entry of said sample into said entry chamber, followed by said second door being closed and said first door being opened to allow entry of said sample into said chamber in which said sample is to be entered, said procedure being reversed to remove said sample said chamber.

4. A spectroscopic ellipsometer or polarimeter system as in claim 3 in which the multiplicity of detector elements are arranged in a selection from the group consisting of:

one-dimensional; and
two-dimensional;
array.

5. A spectroscopic ellipsometer or polarimeter system as in claim 3 which further comprises at least one compensator(s) positioned at a location selected from the group consisting of:
    before said stage for supporting a sample;
    after said stage for supporting a sample; and
    both before and after said stage for supporting a sample;
and in which the spectroscopic ellipsometer or polarimeter system is of the a rotating compensator type.

6. A method of quickly simultaneously taking data at a multiplicity of wavelengths including wavelengths which are, and are not absorbed by environmental components, comprising the steps of:
    a) providing a spectroscopic ellipsometer or polarimeter system comprising a source of a polychromatic beam of electromagnetic radiation, a polarizer, a stage for supporting a sample, an analyzer, a dispersive optics and at least one detector system which comprises a multiplicity of detector elements;
    such that when said spectroscopic ellipsometer or polarimeter is used to investigate a sample present on said stage for supporting a sample, a polychromatic beam of electromagnetic radiation produced by said source of a polychromatic beam of electromagnetic radiation is caused to pass through said polarizer and interact with a sample on said stage for supporting a sample, then pass through said analyzer, and interact with said dispersive optics such that a multiplicity of essentially single wavelengths are caused to simultaneously enter a corresponding multiplicity of detector elements in said at least one detector system;
    said spectroscopic ellipsometer or polarimeter system further comprising an environmental control chamber in which the spectroscopic ellipsometer or polarimeter is contained, said environmental control chamber being characterized by a selection from the group consisting of:
        it comprises one chamber region in which is present a polarization state generator comprising components prior to said sample, said sample, and a polarization state detector comprising components after said sample;
        it comprises three chamber regions, in one of which is present a polarization state generator comprising all components prior to said sample, in the second of which is present the sample and in the third of which is present a polarization state detector comprising components after said sample;
        it comprises two chamber regions, in one of which is present a polarization state generator comprising components prior to said sample and said sample, and in the second of which is present a polarization state detector comprising components after said sample;
        it comprises two chamber regions, in one of which is present a polarization state generator comprising components prior to said sample, and in the second of which is present said sample and a polarization state detector comprising components after said sample;
    said spectroscopic ellipsometer or polarimeter system further comprising means for entering a sample into said environmental control chamber in which said sample is present which comprises first and second doors, such that in use the first door is closed to secure the chamber in which a sample is placed, and the second door is opened to allow entry of said sample into said entry chamber, followed by said second door being closed and said first door being opened to allow entry of said sample into said chamber in which said sample is to be entered, said procedure being reversed to remove said sample said chamber;
    b) placing a sample on said stage for supporting a material system and at least partially purging or evacuating said environmental control chamber;
    c) causing said source of polychromatic beam of electromagnetic radiation to provide a polychromatic beam of electromagnetic radiation and causing said beam to interact with said material system on said stage for supporting a sample, and interact with said dispersive optics such that a multiplicity of essentially single wavelengths are caused to simultaneously enter a corresponding multiplicity of detector elements in said at least one detector system.

7. A method of quickly simultaneously taking data at a multiplicity of wavelengths as in claim 6 in which the step of providing at least one detector system which comprises a multiplicity of detector elements involves providing a selection from the group consisting of:
    one-dimensional; and
    two-dimensional;
array.

8. A spectroscopic ellipsometer or polarimeter system comprising a source of a polychromatic beam of electromagnetic radiation, a polarizer, a stage for supporting a sample, an analyzer, a dispersive optics and at least one detector system which comprises a multiplicity of detector elements arranged in a selection from the group consisting of a:
    one-dimensional; and
    multi-dimensional;
array, such that when said spectroscopic ellipsometer or polarimeter is used to investigate a sample present on said stage for supporting a sample, a polychromatic beam of electromagnetic radiation produced by said source of a polychromatic beam of electromagnetic radiation is caused to pass through said polarizer, interact with a sample on said stage for supporting a sample, pass through said analyzer and interact with said dispersive optics such that a multiplicity of essentially single wavelengths are caused to simultaneously enter a corresponding multiplicity of detector elements in said at least one detector system;
said spectroscopic ellipsometer or polarimeter system further comprising an environmental control chamber in which the spectroscopic ellipsometer or polarimeter is contained, said environmental control chamber being characterized by a selection from the group consisting of:
    it comprises one chamber region in which is present a polarization state generator comprising components prior to said sample, said sample, and a polarization state detector comprising components after said sample;
    it comprises three chamber regions, in one of which is present a polarization state generator comprising components prior to said sample, in the second of which is present the sample and in the third of which is present a polarization state detector comprising components after said sample;
    it comprises two chamber regions, in one of which is present a polarization state generator comprising components prior to said sample and said sample, and in the second of which is present a polarization state detector comprising components after said sample;

it comprises two chamber regions, in one of which is present a polarization state generator comprising components prior to said sample, and in the second of which is present said sample and a polarization state detector comprising components after said sample;

said chamber in which is present said sample further comprising means for entering and removing said sample without substantially affecting the environment therewithin.

9. A spectroscopic ellipsometer or polarimeter system as in claim 8 which further comprises at least one compensator present at least one location selected from the group consisting of:

before said stage for supporting a sample; and after said stage for supporting a sample.

* * * * *